(12) United States Patent
Ferguson et al.

(10) Patent No.: US 6,998,057 B2
(45) Date of Patent: Feb. 14, 2006

(54) METHOD FOR MONITORING AND CONTROLLING CHLORINE LEVELS IN AN AQUEOUS MEDIUM

(75) Inventors: Richard H. Ferguson, Cecil Township, Washington County, PA (US); Louis E. Colonna, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 136 days.

(21) Appl. No.: 10/767,929

(22) Filed: Jan. 29, 2004

(65) Prior Publication Data

US 2004/0211731 A1  Oct. 28, 2004

Related U.S. Application Data

(60) Provisional application No. 60/457,497, filed on Mar. 25, 2003.

(51) Int. Cl.
  *C02F 1/76*  (2006.01)
(52) U.S. Cl. ............. 210/739; 210/754; 210/756; 210/764; 210/198.1; 422/263
(58) Field of Classification Search ............... 210/739, 210/754, 756, 764, 198.1; 422/263
  See application file for complete search history.

(56) References Cited

U.S. PATENT DOCUMENTS

| | | | |
|---|---|---|---|
| 4,323,092 A | 4/1982 | Zabel ..................... 137/5 |
| 5,089,127 A | 2/1992 | Junker et al. ............ 210/206 |
| 5,324,665 A | 6/1994 | Lessard .................... 436/55 |
| 5,384,102 A | 1/1995 | Ferguson et al. ......... 422/264 |
| 5,427,748 A | 6/1995 | Wiedrich et al. ......... 422/264 |
| 5,447,641 A | 9/1995 | Wittig ...................... 210/756 |
| 5,611,937 A | 3/1997 | Jarocki .................... 210/754 |
| 5,629,212 A | 5/1997 | Herman et al. .......... 436/125 |
| 5,637,230 A * | 6/1997 | Billings .................... 210/739 |
| 5,960,808 A | 10/1999 | Ferguson et al. ............ 137/5 |
| 6,138,703 A | 10/2000 | Ferguson et al. ............ 137/1 |
| 6,298,871 B1 | 10/2001 | Pickens et al. ........... 137/268 |
| 6,544,487 B1 | 4/2003 | Ferguson et al. ......... 422/261 |
| 6,838,007 B1 * | 1/2005 | Marmo et al. ........... 210/754 |

* cited by examiner

*Primary Examiner*—Robert A. Hopkins
(74) *Attorney, Agent, or Firm*—Linda Pingitore

(57) ABSTRACT

A method for monitoring and adjusting the level of free chlorine in an aqueous fluid is described. In the described method, first aqueous fluid (50) substantially free of free chlorine is introduced into a suitable mixing vessel (26) wherein it contacts a solid chemical material that is a source of free chlorine and chloride ion. Second aqueous fluid (58) containing free chlorine and chloride ion is removed from the mixing vessel and forwarded to a holding tank (10). The chloride ion concentration of second aqueous fluid in the holding tank is measured by a chloride ion specific sensor in probe housing (22), which sensor is in electrical contact with microprocessor (30). Microprocessor (30), in response to the chloride ion measurement, sends an output signal to valve control means 44, which if necessary increases or decreases the flow of first aqueous fluid into mixing vessel (26). Second aqueous fluid in holding tank (10) is forwarded by pump means (20) to the point of application.

35 Claims, 2 Drawing Sheets

METHOD FOR MONITORING AND CONTROLLING CHLORINE LEVELS IN AN AQUEOUS MEDIUM

CROSS REFERENCE TO RELATED APPLICATIONS

This application claims the benefit of U.S. Provisional Application No. 60/457,497 filed Mar. 25, 2003.

BACKGROUND OF THE INVENTION

Description of the Invention

The present invention is directed to a method for monitoring and adjusting the level of free available chlorine in an aqueous medium. In particular, the method of the present invention makes use of a chloride ion specific sensor to control the amount of free available chlorine present in an aqueous medium containing free chlorine and chloride ion. The present invention is also directed to a method of sanitizing surfaces, which method comprises contacting a surface, article or object in need of sanitizing with an aqueous medium containing free available chlorine, wherein the concentration of free available chlorine in the aqueous medium is controlled by the aforedescribed method. The present invention is further directed to treating an aqueous medium that requires sanitizing by adding to such aqueous medium an aqueous fluid containing free available chlorine, the concentration of which is controlled by the aforedescribed method.

The controlled addition of a source of free available chlorine to an aqueous medium in order to establish a desired level of free or "active" chlorine therein is useful in many applications. The presence of appropriate amounts of free available chlorine in an aqueous medium serves to eradicate deleterious amounts of pathogenic microorganisms, such as viruses and bacteria that may be present therein. Ingestion of or even topical exposure to unsanitized or inadequately sanitized water containing pathogens, such as bacteria, can lead to sickness and disease in animals and humans. Further, ingestion by animals and humans of unsanitized or inadequately sanitized foods, or foods that have been processed on unsanitized or inadequately sanitized surfaces, e.g., harvested fruits and poultry products, can lead to sickness and disease in animals and humans.

Drinking water typically contains from 0.5 to 1 part free available chlorine (FAC) per million parts of water (ppm). Recreational bodies of water, e.g., swimming pools, hot tubs, spas, etc., typically contain from 1 to 3 ppm of FAC. Water having a FAC content in amounts of greater than 10 ppm can be used to sanitize surfaces or articles to which it is applied, and can be used to sanitize liquid media to which it is added. Free available chlorine can be introduced into water by adding a source of hypochlorous acid (HOCl) or hypochlorite anion (ClO—) into the water.

Controlling the amount of free available chlorine in an aqueous stream or body of water is important. For example, if too much FAC is present in drinking water, it will become undrinkable. Similarly, ingestion of drinking water containing too little FAC can lead to sickness. If too little FAC is present in an aqueous fluid that is to be used for sanitizing a surface, e.g., by spray application, the surface may not be adequately sanitized, which can lead to the contamination of food processed on such surfaces.

A common method of controlling the amount of free available chlorine in an aqueous stream involves analysis of the aqueous stream using oxidation-reduction potential (ORP) analysis. Typically, this involves passing the aqueous fluid in which FAC is present past a pair of electrodes. The electrodes develop an electrical potential, which is related to the amount of FAC present in the aqueous stream—the relationship being indicated mathematically by the Nernst equation. The amount of FAC detected dictates whether more or less FAC (or FAC producing substance) is added to the aqueous fluid. Oxidation-reduction potential analysis becomes less sensitive and unreliable when the FAC content of an aqueous fluid or body of water exceeds 2 ppm, especially when the FAC content exceeds 10 ppm. Further, the ORP method requires that the pH of the water being analyzed be continuously measured or controlled, which adds to the cost and maintenance of this method.

Another method of controlling the amount of free available chlorine present in water involves regulating the flow rate of the water passing through a chlorination unit containing a source of free available chlorine. The flow rate is calibrated based on a previously determined correlation between different flow rates and the resulting amounts of FAC present in the solution discharged from the chlorination unit. The manufacturer of the chlorination unit typically supplies such correlation data. A drawback of such a method is that it can be unreliable. In particular, if the operating efficiency of the chlorination unit drifts or degrades with time, either too much or too little of the chemical source of FAC will be added to the water passing through the chlorination unit.

U.S. Pat. No. 4,323,092 discloses an apparatus and process for measuring and monitoring the free active chlorine content of an aqueous solution, e.g., drinking or bathing water. The apparatus utilizes a measuring cell, which measures the amount of free active chlorine by an amperometric or coulometric process. The measuring cell is connected to an electrical comparison circuit, which controls a regulator or magnetic valve, in order to control the amount of active chlorine in the system.

U.S. Pat. No. 5,447,641 discloses a poultry water chlorinator and a method of using it. An in line chlorination unit having solid calcium hypochlorite contained within the unit is provided. Water introduced into the chlorination unit dissolves the solid calcium hypochlorite. The resulting calcium hypochlorite solution is diluted to a desired concentration, and then dispensed at a flow rate in the range of approximately 50 to 3500 US gallons/day (0.2 to 13.25 cubic meters/day).

U.S. Pat. No. 5,611,937 discloses a method and apparatus for treating water in which water from a local supply is mixed with measured quantities of a chlorine disinfectant and introduced into a holding vessel. Carbon dioxide is also added to the holding vessel. A treating module, having a flow sensor therein, is governed by a microprocessor, which controls the mixing of the chlorine disinfectant and water.

U.S. Pat. No. 5,324,665 discloses a method for monitoring automatically the chloride content in a fluid stream in an oil refinery. In the described method, a sulfide scavenger is added to a sample of the fluid stream in order to react with sulfide that is present in the stream to create a sulfide reaction product. The resulting fluid is passed through a membrane that prevents the sulfide reaction product from passing through it, and the fluid passing through the membrane is passed to a measurement cell that includes a chloride specific electrode, which measures the chloride content of the fluid. The result of such measurement is used to control the amount of neutralizing agent added to the fluid stream.

U.S. Pat. No. 5,629,212 discloses a process for analyzing the chloride content of process waters containing sulfides, hydrocarbons and chloride. The process comprises the steps of: (a) stripping hydrocarbons and hydrogen sulfide from a batch of the liquid, (b) reacting the liquid batch with an oxidizing reagent to oxidize the sulfhydrate (HS—) and sulfur (S—) ions into sulfate ions and to lower the pH of the liquid to be analyzed, and (c) then analyzing the chloride content by ionometry.

U.S. Pat. No. 5,960,808 discloses a method of controlling the amount of free available chlorine in an aqueous medium by measuring the conductivity of the aqueous medium before and after a source of free chlorine is added to the aqueous medium. In response to such measurement, the amount of the source of free chlorine added to the aqueous medium is adjusted. The use of conductivity as a means to control the amount of free available chlorine in an aqueous medium is not totally reliable because air bubbles produced by the mixing and movement of the various fluid streams involved interfere with the conductivity measurement.

It would be desirable to have a relatively simple, cost effective, reliable and accurate method of controlling the amount of free available chlorine in an aqueous medium, particularly amounts of free available chlorine that are present in amounts of in excess of 10 parts per million (ppm). Aqueous media containing free available chlorine are used to sanitize swimming pools, spas and other recreational bodies of water, to treat cooling water, wastewater and drinking water, and to sanitize surfaces used in the preparation of food and beverages, as well as the food itself in certain cases.

In accordance with the present invention there is provided a method of monitoring and adjusting free available chlorine levels present in an aqueous fluid or medium. In one embodiment, the present invention relates to a method for controlling the level of free available chlorine in an aqueous fluid comprising the steps of:

(a) providing a first aqueous fluid that is substantially free of free available chlorine;

(b) providing water-soluble material, which is a source of free available chlorine and chloride ion;

(c) admixing said first aqueous fluid with water-soluble material, thereby to produce a second aqueous fluid containing free available chlorine and chloride ion;

(d) measuring the level of chloride ion in said second aqueous fluid by means of a chloride ion specific sensor; and (e) controlling, if necessary, in response to the measurement of step (d) the level of free chlorine in said second aqueous fluid by the further steps of (i) adjusting the amount of first aqueous fluid admixed with said water-soluble material, (ii) diluting said second aqueous fluid with aqueous fluid substantially free of free available chlorine, or (iii) a combination of steps (i) and (ii).

In a further embodiment, the present invention relates to a method for controlling the amount of free chlorine in an aqueous fluid comprising the steps of:

(a) providing a first aqueous fluid that is substantially free of free chlorine;

(b) providing a water-soluble material that is a source of free chlorine and chloride ion in a mixing vessel;

(c) introducing first aqueous fluid into said mixing vessel, thereby to admix said first aqueous fluid with water-soluble material that is a source of free chlorine and chloride ion, thereby to produce second aqueous fluid containing free available chlorine and chloride ion;

(d) removing second aqueous fluid from said mixing vessel;

(e) analyzing for the amount of chloride ion in second aqueous fluid removed from said mixing vessel by means of a chloride ion specific sensor; and (f) controlling, if necessary, in response to the analysis of step (e) the amount of free chlorine in said second aqueous fluid around a pre-selected value by the further steps of (i) adjusting the rate at which first aqueous fluid is introduced into said mixing vessel, (ii) adding aqueous fluid substantially free of free chlorine to the second aqueous fluid, or (iii) a combination of steps (i) and (ii).

In accordance with another embodiment of the present invention there is provided a method of monitoring and adjusting the level of free available chlorine in an aqueous fluid, comprising the steps of:

(a) providing in a mixing vessel a water-soluble material that is a source of free available chlorine and chloride ion;

(b) providing a first aqueous fluid substantially free of free chlorine;

(c) introducing controllably first aqueous fluid into said mixing vessel and into contact with the water-soluble material, thereby to produce second aqueous fluid containing free chlorine and chloride ion;

(d) withdrawing second aqueous fluid from said mixing vessel and forwarding second aqueous fluid to a holding vessel;

(e) measuring the level of chloride ion in second aqueous fluid contained in said holding vessel by means of a chloride ion specific electrode; and (f) controlling, if necessary, in response to the measurement of step (e) the level of free chlorine in second aqueous fluid in said holding vessel by the further steps of (i) adjusting the rate at which first aqueous fluid is introduced into said mixing vessel, (ii) diluting second aqueous fluid in said holding vessel with aqueous fluid substantially free of free chlorine, or a combination of steps (i) and (ii).

In a further embodiment of the present invention there is provided a method of sanitizing the surface of an article or object with a free chlorine-containing aqueous fluid comprising the steps of:

(a) controlling the amount of free available chlorine present in an aqueous fluid by the steps of:
  (i) providing a mixing vessel having stored therein a water-soluble material that is a source of free available chlorine and chloride ion;
  (ii) providing a first aqueous fluid that is substantially free of free available chlorine;
  (iii) introducing controllably said first aqueous fluid into said mixing vessel, thereby to contact first aqueous fluid with water-soluble material and produce second aqueous fluid containing free available chlorine and chloride ion;
  (iv) removing second aqueous fluid from said mixing vessel;
  (v) forwarding second aqueous fluid to a holding vessel;
  (vi) measuring the level of chloride ion in second aqueous fluid present in the holding vessel using a chloride ion specific electrode; and
  (vii) controlling, if required, in response to the measurement of step (a)(vi) the level of free available chlorine in second aqueous fluid in the holding vessel by the controlled steps of [a] adjusting the rate at which first aqueous fluid is introduced into said mixing vessel,[b] introducing first aqueous fluid substantially free of free chlorine directly into said holding vessel or by a combination of steps [a] and [b]; and (b) applying second aqueous fluid from said holding vessel to a surface or object to be sanitized.

In still further contemplated embodiments of the present invention, the second aqueous fluid containing the controlled levels of free chlorine and chloride ion can be used to treat various aqueous media, including such aqueous media as recreational bodies of water, e.g., swimming pools and spas, drinking water, wastewater, and water used for cooling, e.g., cooling tower water.

The features that characterize the present invention are pointed out with particularity in the claims that are annexed to and form a part of this disclosure. These and other features of the invention, its operating advantages and the specific objects obtained by its use will be more fully understood from the following detailed description and the accompanying drawings in which a particular embodiment of the invention is illustrated and described.

Other than in the operating examples, or where otherwise indicated, all numbers expressing quantities of constituents used in the specification and claims are to be understood as modified in all instances by the term "about".

DETAILED DESCRIPTION OF THE INVENTION

Figure 1:
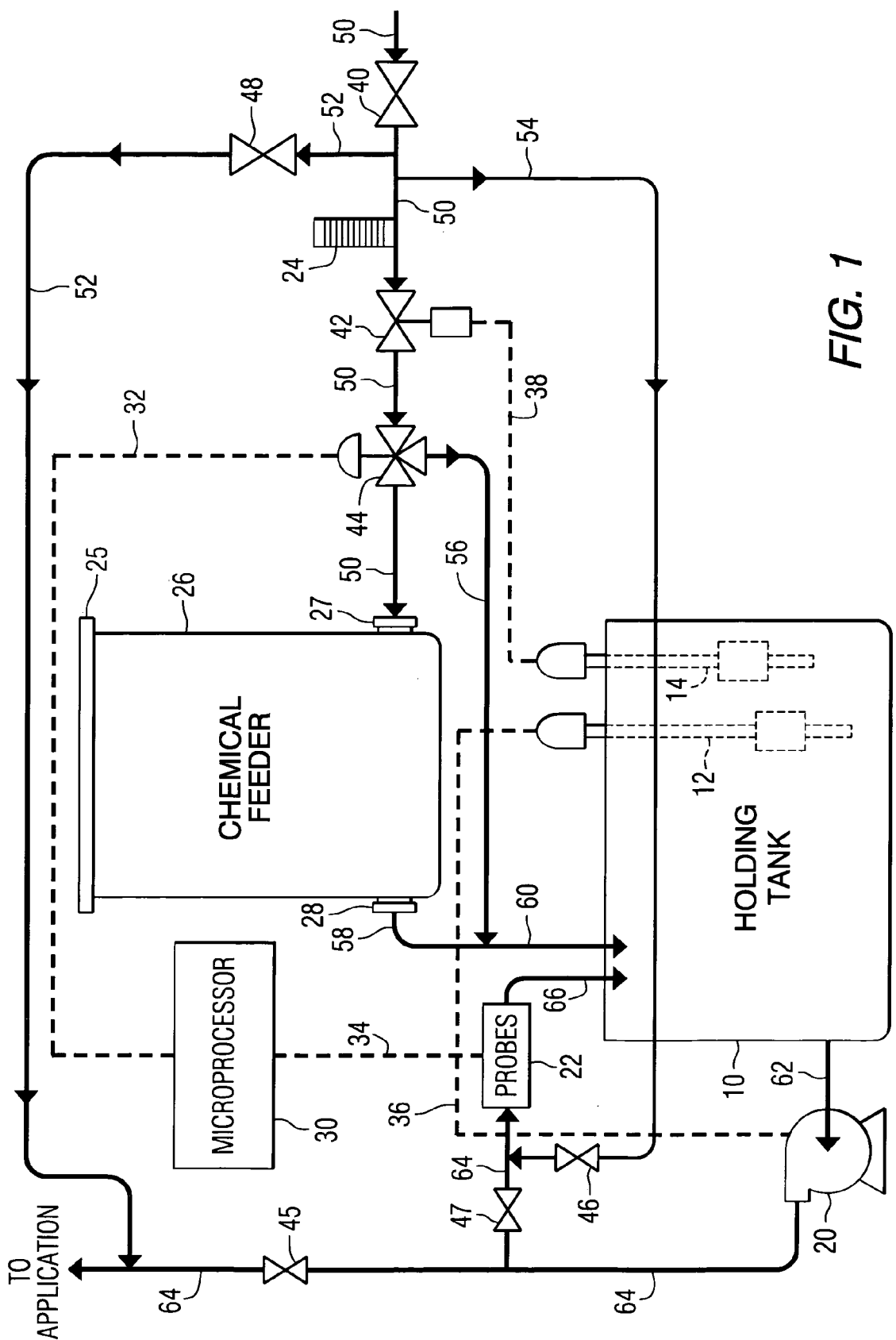
FIG. 1 is a schematic representation of an embodiment of a system incorporating the method of the present invention.

In describing embodiments of the present invention represented by FIG. 1, specific elements and terminology are employed for the sake of clarity. However, the invention is not intended to be limited to those specific elements and terminology, it being understood that each specific element includes all other technical equivalents that function in a similar manner to accomplish a similar or equivalent purpose.

Referring now to FIG. 1 of the drawings, there is shown a schematic of a particular embodiment of a system of the present invention wherein an aqueous fluid, such as water, and solid alkaline earth metal hypochlorite, such as calcium hypochlorite, are used. As shown in FIG. 1, water from a local supply (not shown) is introduced into the system by means of conduit 50. Such water is substantially free of free chlorine, but may contain chloride ion—usually as a result of chemical treatment during a purification process, or if the chloride ion is naturally occurring, e.g., in well water. The water flows through valve means 40, flow meter 24, solenoid valve 42, three-way valve means 44 and thence through fluid inlet means 27 into chemical feeder 26. Valve means 40 can be used to regulate the flow rate of water to the system or to shut off all flow of water to the system from the local supply, thereby isolating the system from that source of water. Flow meter 24 measures the flow rate of water being introduced into the system, which flow rate can be adjusted by valve 40. Solenoid valve 42 is connected electrically to low/high level switch 14. Switch 14 is a float and magnetic read switch. Such switch type is commercially available and is known to those skilled in the art, e.g., the Liquistat Liquid Level Controller or the Flowline Smart Trak switch. Three-way valve means 44 can be a George Fischer three-way polyvinyl chloride electrically actuated ball valve. While shown as a three-way valve, valve means 44 can be a pneumatically controlled valve, or two 2-way valves to accomplish the same result can replace it.

By-pass line 54 and valve means 46 allow incoming source water to be sent periodically to probe housing 22 to check the level of chloride ion in the incoming source water in order to adjust the set point at controller means 30. By-pass line 52 allows incoming source water to by-pass the system entirely, thereby allowing the source water to be forwarded to the point of application. Valve means 48 controls the flow of source water through by-pass line 52. Valve means 48 is normally in a closed position. Valve means 45 in line 64 is usually in an open position, but will be closed to allow incoming source water to be forwarded directly to the point of application by means of conduit 52.

Chemical feeder unit 26 is a mixing vessel that is suitable for admixing the aqueous fluid, e.g., water, entering the system through conduit 50 and a water-soluble chemical material that is a source of free available chlorine and chloride ion. The particular structure of chemical feeder unit 26 is not a critical feature of the present invention. It can be any vessel known to those skilled in the art that will permit the mixing of the water-soluble material that is the source of free chlorine and chloride ion and the aqueous fluid, e.g., water, in which that material is dissolved. Examples of such vessels include those described in U.S. Pat. Nos. 3,595,395, 4,584,106, 4,732,689, 4,842,729, 5,089,127, 5,384,102, 5,427,748, 5,441,711, 5,447,641, 5,932,093 and 6,298,871, and similar vessels shown in other patents referred to in these identified patents.

In one embodiment of the present invention, feeder unit 26 is a low-pressure chlorination unit. Feeder unit 26 can be a high pressure or pressurized unit, if desired. Further, the mixing vessel can be a pipe or conduit in which the aqueous fluid, e.g., water, is mixed with an aqueous solution of the aforementioned water-soluble chemical material, such as calcium hypochlorite, sodium hypochlorite or chloride ion-containing hypochlorous acid.

Water-soluble chemical material that can be used as a source of free chlorine and chloride ion can be a liquid or solid, and can be inorganic or organic. Liquid inorganic sources include alkali metal hypochlorite, such as sodium hypochlorite, potassium hypochlorite and lithium hypochlorite, concentrated aqueous solutions of alkaline earth metal hypochlorite, such as calcium hypochlorite, and hypochlorous acid that contains chloride ion. Solid inorganic sources include lithium hypochlorite, and alkaline earth metal hypochlorites, such as calcium hypochlorite, barium hypochlorite and strontium hypochlorite. All of the foregoing liquid and solid inorganic hypochlorite sources of free chlorine and chloride ion are well known and, if not readily commercially available, can be prepared by methods know to those skilled in the art. For example, alkali metal hypochlorites, such as sodium hypochlorite, can be prepared by the reaction of the corresponding alkali metal hydroxide, e.g., sodium hydroxide, with chlorine or hydrogen chloride. Commercial sources of sodium hypochlorite typically contain from 12 to 15% available chlorine. Chloride ion-containing hypochlorous acid can be prepared by chlorine hydrolysis, e.g., by reacting chlorine (liquid or gaseous) with water or an aqueous base such as sodium hydroxide.

Solid organic sources include chloride ion-containing halo-substituted hydantoins, e.g., bromo-chloro dimethyl hydantoins and dichlorohydantoin, the chlorinated isocyanurates, including trichloroisocyanurate, dichloroisocyanurate and the alkali metal, e.g., sodium and potassium, salts of the dichloroisocyanurate. The halo-substituted hydantoins and chlorinated isocyanurates are commercially available or can be prepared by methods known to those skilled in the art. These organic source materials, as conventionally prepared, do not typically contain chloride ion. However, they can be adapted to contain chloride ion by adding a chloride ion-containing compatible material, e.g., sodium chloride, to the material before being formed into a solid form, e.g., tablet. By this technique, chloride ion-containing halo-substituted hydantoins and chloroisocyanurates useful in the method of the present invention can be prepared.

Chemical feeder unit 26 is provided with at least one water-soluble solid chemical material, e.g., an inorganic or organic chemical material, that is a source of free chlorine and chloride ion. In the embodiment described in FIG. 1 and the Examples, solid calcium hypochlorite is used to provide the source of free available chlorine. The calcium hypochlorite (not shown in FIG. 1), is usually in the form of tablets or similar solid forms, and is charged to feeder unit 26, through a port (not shown) in unit 26, or through removable lid 25. By "water-soluble" is meant that the chemical material is sufficiently soluble in water at ambient conditions to produce an aqueous solution that contains free chlorine at a concentration sufficient for its intended use, i.e., sanitizing use.

By the interchangeable terms "free chlorine" and "free available chlorine" is meant chlorine that is present in an aqueous solution in an oxidized form. Free available chlorine (FAC) can be present in the form of hypochlorous acid (HOCl) and/or hypochlorite anion (ClO—). The chlorine atom is in a +1 oxidation state. By chloride ion is meant the chloride anion (Cl—).

Figure 2:
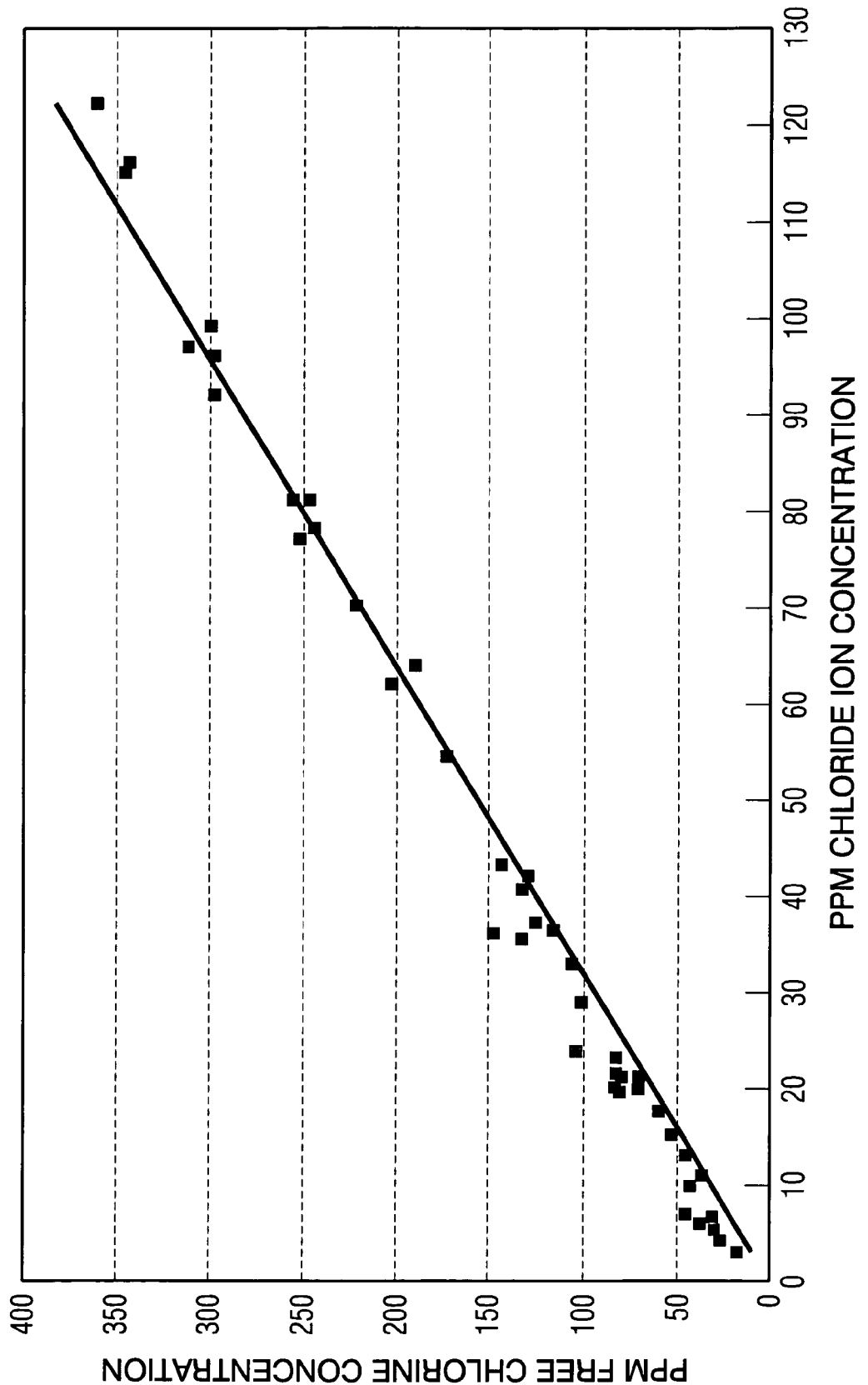
FIG. 2 is a graph showing a plot of the amount of free available chlorine present in aqueous solution (in ppm) vs. the amount of chloride ion present in that aqueous solution (in ppm) for commercially available solid calcium hypochlorite.

The ratio of free available chlorine to chloride ion in aqueous solution for materials that are a source of free available chlorine and chloride ion, such as alkaline earth metal hypochlorites, e.g., calcium hypochlorite, is relatively constant. While the ratio may differ for each particular product of manufacture, it can be determined easily by measuring the free available chlorine content of such aqueous solutions at different chloride ion concentrations. This feature, i.e., the relatively constant ratio of free chlorine to chloride ion, permits control of the free chlorine level in an aqueous fluid by measurement of the chloride ion level therein. FIG. 2 is a graph of the amount of free available chlorine versus chloride ion (in parts per million [ppm]) in an aqueous solution prepared from solid calcium hypochlorite tablets. Graphs, such as depicted in FIG. 2, can be produced for any aqueous solution of the aforedescribed organic and inorganic sources of free chlorine and chloride ion, e.g., an alkaline earth metal hypochlorite, e.g., calcium hypochlorite, to be charged to feeder unit 26, aqueous solutions of alkali metal hypochlorites, e.g., sodium hypochlorite, and chloride ion-containing hypochlorous acid.

Aqueous fluid, e.g., water, introduced into feeder unit 26 by means of conduit 50 and fluid inlet means 27 is admixed with water-soluble material that is the source of free available chlorine and chloride ion contained in feeder unit 26, thereby to form an aqueous solution containing free available chlorine and chloride ion. The concentration of free available chlorine and chloride ion in the solution will depend on various factors, including such factors as the rate of flow and the amount of aqueous fluid introduced into and withdrawn from the feeder unit, the residence time of the aqueous fluid within the feeder unit, and the quantity and/or surface area of the water-soluble material that is contacted by the aqueous fluid passing through the feeder unit. All of the foregoing factors are to a certain extent dependent on the internal design of the feeder unit.

One skilled in the art can easily and readily determine the flow rate of aqueous fluid into the particular feeder unit to be used that is required to produce a desired concentration of free available chlorine in the solution produced in the feeder unit by conventional titration, e.g., the glacial acetic acid titration method, of solutions prepared at different flow rates. The concentration of free available chlorine in the solution prepared in and removed from the feeder unit will also depend on the age of the solution since the level of available chlorine in such solutions will degrade with time. Therefore, it is suggested that free chlorine-containing solutions prepared in the above-described manner be used reasonably promptly so as to fully utilize the free available chlorine present in the fresh solution.

Some of the aforementioned factors are particularly relevant to the embodiment where the water-soluble material in the feeder unit 26 is a solid, e.g., calcium hypochlorite tablets. When the water-soluble material is a liquid, e.g., aqueous solutions of alkali metal hypochlorite, alkaline earth metal hypochlorite and chloride ion-containing hypochlorous acid, the concentration of the aqueous solution withdrawn from the mixing vessel will depend primarily on the initial concentration of the material charged to the mixing vessel and the amount of aqueous fluid substantially free of free chlorine that is admixed with it.

In the case of aqueous solutions of alkali metal hypochlorite, e.g., sodium hypochlorite, it is contemplated that a mixing vessel, such as depicted in FIG. 1, would not be used; but that a metering pump would be used as the feeder unit. In that case, it is contemplated the alkali metal hypochlorite solution is forwarded by the metering pump into a conduit where it is mixed with aqueous fluid substantially free of free chlorine. The resultant aqueous solution could be forwarded to a holding vessel, such as shown in FIG. 1, or if desired directly to the point of application. The metering pump would be connected electrically to and controlled by controller means, e.g., a microprocessor. Analysis for the chloride ion would occur in the holding vessel or from a sample taken from the conduit downstream of the point of mixing.

In the case of chloride ion-containing hypochlorous acid, it is contemplated that a source of chlorine (liquid or gaseous) would be metered into a mixer-injector device, such as a venturi-type differential pressure mixer injector (which serves as the feeder unit), into which water is also introduced. The resulting aqueous solution of chloride ion-containing hypochlorous acid can be forwarded to a holding tank, as shown in FIG. 1, or directly to the point of application, as described above. Mixer-injectors, such as venturi eductors, e.g., gas injectors, are known to those skilled in the art. See, for example, U.S. Pat. Nos. 4,123,800 and 5,863,128. Such devices are available from the Mazzei Injector Corporation.

The free available chlorine and chloride ion-containing solution (FAC Solution) produced in feeder unit 26 is withdrawn from that unit through fluid outlet means 28 and forwarded by means of conduit 58 to holding tank 10. FAC Solution is withdrawn from holding tank 10 through conduit 62 by means of pump 20 and forwarded by means of conduit 64 through valve means 45 to the end use application.

Fitted to holding tank 10 is Low/High level switch 14, which is electrically connected to solenoid valve 42 by signal conductor 38. Upon initial start-up, the Low/High level switch 14 will open solenoid valve 42 to permit aqueous fluid, e.g., water, to flow through three-way valve means 44, which can direct the aqueous fluid (i) into feeder unit 26, (ii) through conduits 56 and 60 to holding tank 10, or (iii) a combination of (i) and (ii). When the level of fluid in the holding tank 10 reaches the high level set by switch 14, pump 20 will start and valve 42 will shut off the flow of aqueous fluid to the system. When the fluid in holding 10 is drawn down and reaches the Low level of switch 14, valve 42 opens and again allows aqueous fluid to flow into the system. As described, the system operates in a batch mode, rather than in a continuous mode; however, continuous operation of the system is contemplated.

In a contemplated start-up, aqueous fluid is directed through solenoid valve 42 and three-way valve 44 to the chemical feeder unit 26 so that FAC Solution produced in feeder unit 26 fills the holding tank until the high level of switch 14 is reached, at which time valve 42 shuts off the flow of aqueous fluid to valve means 44. Pump 20 then withdraws FAC Solution from holding tank 10 until the low level of switch 14 is reached, at which time valve 42 is opened and allows aqueous fluid to flow through valve means 44 and again enter feeder unit 26 from which FAC Solution is forwarded to holding tank 10. This process is repeated indefinitely until the chemical source material in feeder unit 26 is exhausted, at which time the source material is replenished. In another contemplated mode of operation, aqueous fluid is first directed by valve means 44 to the holding tank until the high level of switch 14 is reached, at which time valve 42 shuts off the flow of fluid to the system. Pump 20 withdraws aqueous fluid from the holding tank until the low level of switch 14 is reached, at which time valve 42 allows aqueous fluid to flow into valve means 44, which then forwards aqueous fluid to feeder unit 26 to produce FAC Solution, which is then forwarded to holding tank 10. When the high level of switch 14 is reached, solenoid valve 42 shuts off the flow of fluid to the system. When pump 20 draws down the liquid in holding tank 10 to the low level of switch 14, valve 42 opens and allows aqueous fluid to flow again through valve means 44 into feeder unit 26, thereby producing FAC Solution, which is then forwarded to holding tank 10. This process continues until the liquid in holding tank 10 is substantially all FAC Solution.

Valve means 44 can direct the flow of aqueous fluid passing through it all (100%) to holding tank 10 or all (100%) to feeder unit 26, and can split the flow of aqueous fluid between the feeder unit and holding tank over many settings between, e.g., 75% to the feeder unit and 25% to the holding tank, i.e., the ratio of the flow of aqueous fluid to the holding tank and the flow of aqueous fluid to the feeder unit can be varied widely. In a further contemplated embodiment, FAC Solution produced in feeder unit 26 is forwarded to holding tank 10 and simultaneously FAC solution in holding tank 10 is withdrawn from holding tank 10 through conduit 62 by means of pump 20 and forwarded by means of conduit 64 to the end use application.

Also fitted to holding tank 10 is Low/Low level switch 12, which is connected electrically by means of signal conductor 36 to pump 20 to avoid pump operation when the level of liquid in holding tank 10 is at or below the level of outlet conduit 62 (or some other level), thereby avoiding pump 20 from running dry. Switch 12 can be the same type of equipment as that described for switch 14. Once the Low/Low level in holding tank 10 is cleared, pump 20 can start and forward aqueous FAC Solution from holding tank 10 to the end use application and to probe housing 22 for measurement of the chloride ion level in the solution.

FAC Solution withdrawn from holding tank 10 is sampled by means of sample line 64, the flow to which is controlled by valve 47. The sampled solution is forwarded to probe housing 22, which contains a chloride ion specific electrode (sensor). In a contemplated embodiment of the present invention, housing 22 contains a triple junction glass electrode for reference and a RTD (resistance temperature detector) probe, e.g., a thermocouple, to correct for temperature fluctuations in addition to the chloride ion specific electrode. Each of the aforementioned probes is known to those skilled in the art and is commercially available. Chloride ion-specific electrodes are available commercially, for example, from Tess-Com, Inc. and Advanced Sensor Technologies, Inc. Particular commercially available chloride ion specific electrode include Tess-Com's model #1940, and the Iotron™ Sensors AB 8110 and AB 6110, which are available from Advanced Sensor Technologies.

The chloride ion specific electrode in probe housing 22 is connected electrically by signal conductor 34 to controller means 30, which can be a microprocessor or programmable logic controller (PLC). Microprocessors useful in the method of the present invention are known to those skilled in the art of instrumentation and control. Controller 30 controls the chloride ion concentration in the FAC Solution in holding tank 10 around a predetermined set point, which is selected based on the desired level of free chlorine required for the end use application. The set point takes into account the base chloride ion level of the aqueous fluid entering the system through valve 40, i.e., the base chloride ion level is subtracted from the chloride ion level measured for any particular FAC Solution to arrive at a true chloride ion increase versus free chlorine in the FAC Solution. Controller 30 receives and analyzes signals from the chloride ion specific electrode by means of signal conductor 34, and in response thereto, if required, (based on the set point previously established) sends an output signal by means of signal conductor 32 to three-way valve means 44.

Valve means 44, in response to control signals from controller means 30, adjusts the rate at which aqueous fluid, e.g., water, is introduced into feeder unit 26, into by-pass line 56, or into both feeder unit 26 and by-pass line 56 to control the chloride ion level (and hence the free chlorine level) of the FAC Solution produced in feeder unit 26 around the predetermined set point. Valve 44, as described, can increase or decrease the flow of aqueous fluid into feeder unit 26. Increasing the rate of aqueous fluid, e.g., water, introduced into feeder unit 26 increases the rate at which a solid water-soluble chemical source of free chlorine and chloride ion stored in the feeder unit is dissolved, thereby increasing the amount of chloride ion in the aqueous FAC Solution produced in the feeder unit (and hence increasing the amount of free chlorine in the FAC Solution forwarded to holding tank 10). Conversely, decreasing the rate of aqueous fluid, e.g., water, introduced into feeder unit 26, decreases the rate at which a solid water-soluble chemical source of free chlorine and chloride ion stored in feeder unit 26 is dissolved, thereby decreasing the level of chloride ion in the aqueous FAC Solution produced in the feeder unit (and hence decreasing the amount of free chlorine in the FAC Solution forwarded to holding tank 10).

Valve means 44 can also divert aqueous fluid from the supply source (not shown) directly to holding tank 10 by means of conduits 56 and 60 to dilute the FAC Solution contained in holding tank 10 if the chloride ion level in that solution is too high. A combination of increasing or decreasing the rate of aqueous fluid introduced into feeder unit 26, and dilution of the FAC Solution in holding tank 10 with source aqueous fluid is contemplated. Since the concentrations of free chlorine and chloride ion in the FAC Solution produced in feeder unit 26 are proportional one to the other, increasing or decreasing the concentration of one in feeder unit 26 also increases or decreases the other proportionately. Hence, as used herein, reference can be made to increasing or decreasing the concentration of free chlorine or chloride ion in the FAC Solution (without dilution) interchangeably.

By-pass line 54 allows aqueous fluid, such as water from the local source, to be introduced into line 64 in order to determine the base chloride ion level of the aqueous fluid introduced into the system through valve means 40. Fluid entering line 64 by means of conduit 54 is controlled by valve 46. Valve 47 will be closed while valve 46 is in an open position in order to take such base chloride ion readings. Fluid entering probe housing 22, whether from line 54 or sample line 64 is forwarded from probe housing 22 to holding tank 10 through line 66.

Controller means 30 and other electrically powered equipment, e.g., pump 20, are connected to an external power source, not shown. Controller means 30 can include an output device to display the values determined by it, which may be one or both of a printer, cathode ray tube display, or digital display. Controller 30, in response to the analysis of the chloride ion specific sensor, sends a valve control signal to valve means 44 by signal conductor 32. Valve means 44, which can be an electrically actuated control valve, is adjusted in response to the output valve control signal (as described above), thereby controlling the level of chloride ion in tank 10. In one embodiment of the present invention, controller means 30 is a Rosemount Model 54e pH/ORP Analyzer/Controller, which has been reconfigured by the manufacturer, Rosemount Analytical Inc. of Irvine, Calif. to measure the chloride ion level of the FAC Solution.

In a particular embodiment of the present invention, the chemical source of free chlorine and chloride ion is selected from the group consisting of calcium hypochlorite, sodium hypochlorite, lithium hypochlorite, chloride ion-containing hypochlorous acid, chloride ion-containing halo-substituted hydantoins, and chloride ion-containing chlorinated isocyanurates. In a typical embodiment of the present invention, such chemical source is calcium hypochlorite, and the feeder unit is a chlorination unit, i.e., a unit wherein a solid chemical source of free chlorine and chloride ion is dissolved in an aqueous medium, e.g., water. When the chemical source is a solid at ambient conditions, i.e., standard conditions of temperature and pressure (STP), the form and size of the solid chemical can vary, e.g., pellets, cylinders and tablets. Such forms can be readily prepared by art-recognized forming techniques, e.g., tableting equipment. The solid form should not be so dense as to prevent it from being readily soluble in the aqueous dissolving fluid used to prepare the FAC Solution.

In one embodiment of the present invention, the level of free available chlorine (FAC) produced in feeder unit 26 is at least 5 parts FAC per million parts of FAC solution (ppm), typically at least 30 ppm, more typically at least 50 ppm, e.g., from 100 to 300 ppm. In a further embodiment of the present invention, the level of FAC produced in feeder unit 26 is at least 1000 ppm, e.g., at least 5000 ppm, and still more particularly at least 10,000 ppm. Even higher levels of FAC, e.g., 100,000 ppm, are contemplated. The level of FAC in the FAC Solution can range between any of the recited minimum and maximum values, inclusive of the minimum and maximum values.

Feeder unit 26 may be any appropriate unit suitable for preparing FAC Solutions in a substantially reproducible manner. In a particular embodiment of the present invention, feeder unit 26 is a chlorination unit, as described in U.S. Pat. No. 5,384,102, the disclosure of which is incorporated herein in its entirety. The FAC or source of FAC can be present within or introduced into feeder unit 26, through a port (not shown) or removable lid 25.

Feeder unit 26 and holding tank 10 and their various components will be fabricated from any suitable material of construction or combinations of such materials that are chemically and corrosion resistant to the source of available chlorine charged to the feeder unit. Examples of suitable materials of construction include, but are not limited to, polyethylene, ABS (acrylonitrile-butadiene-styrene resin), fiberglass reinforced resins, polystyrene, polypropylene, poly(vinyl chloride) [PVC], chlorinated poly(vinyl chloride) or any other appropriate material(s) that is chemically resistant to aqueous solutions containing free available chlorine and chloride ion. Other materials such as stainless steel may also be used, but the use of such material would result in a substantial increase in the cost of such vessels. Typically, the feeder unit and holding tank are fabricated from poly(vinyl chloride) [PVC}, which is generally chemically resistant to such aqueous solutions. Parts of the feeder unit can be fabricated by art-recognized methods, including for example, injection or rotation molding. Further, surfaces of pumps, valves, switches, conduits, etc. exposed to the chlorine-containing solutions handled by the system will also be fabricated from materials of construction resistant to the corrosive FAC Solution.

When constructed of plastic resin material, the various parts of the feeder, holding tank, etc. may be joined together by solvent, thermal welding, cementing, e.g., by use of PVC cement, or by threading. Inlet and outlet conduits and fittings may be joined together by the use of conventional bulkhead fittings. If a metal, such as stainless steel is used, conventional welding of the parts may be used to join parts together. Alternatively, the various parts can be joined together by conventional threaded bolts and with appropriate gasketing to insure that connections are sealed, i.e., water tight.

The present invention is also directed to a method of sanitizing a surface of an article or object, or to treatment of aqueous media requiring sanitizing. With reference to FIG. 1, the FAC Solution forwarded through conduit 64 can be delivered to a further holding tank downstream (not shown) or to one or more spray nozzles (not shown) for ultimate use. The FAC Solution is a fluid that can be used as a sanitizing solution, which can be applied to a surface or object to be sanitized, or it can be introduced into a liquid media, e.g., cooling water.

The FAC Solution can be applied to an object that requires sanitizing by any appropriate method, examples of which include but are not limited to: spray application; wiping with soaked rags; curtain or waterfall application; and soaking by immersion. Non limiting examples of surfaces or articles which may be sanitized by the method of the present invention include, but are not limited to: harvested vegetables such as potatoes, sweet potatoes, and mushrooms; harvested fruits, such as apples; metal surfaces in food processing plants, e.g., meat processing plants, or other metal surfaces that require sanitizing; equipment in breweries, e.g., fermenting tubs, and the interior and exterior of pipes; and meat products, e.g., chicken carcasses in chicken processing plants. Non-limiting examples of liquid media requiring sanitizing include, but are not limited to, drinking water, wastewater, cooling water, and recreational bodies of water, e.g., swimming pools and spas.

The present invention is more particularly described in the following examples, which are intended to be illustrative only, since numerous modifications and variations therein will be apparent to those skilled in the art. Unless otherwise specified, all parts and percentages are by weight.

EXAMPLE I

Run 1

This example describes use of a chloride ion specific electrode to measure the level of chloride ion in an aqueous fluid produced in a feeder unit that generates an aqueous solution containing free available chlorine and chloride ion. The chloride ion concentration is calibrated to the free chlorine concentration, which allows control of the free chlorine concentration in the aqueous fluid by measurement of the chloride ion concentration.

A 22 US gallon (0.08 cubic meters) tank was fitted with a PVC Kerrick float valve and a submersible pump to remove aqueous solution from the tank. The tank measured 24 inches long×12 inches wide×12 inches high (61 cm×30.5 cm×30.5 cm). A chemical feeder unit similar to that described in U.S. Pat. No. 6,298,871 was mounted above and to the side of the tank. The discharge from the feeder unit was fitted with a pipe T to allow water from the float valve to mix with the discharge from the feeder unit to effect proper mixing. The submersible pump had a valve on the discharge line to maintain a constant flow. Source water from the public utility was used.

Water was allowed to flow through the float valve to fill the tank and the submersible pump discharge flow was adjusted to maintain a constant level in the tank. Water could also be diverted through the feeder unit by means of a George Fischer ½ inch (1.27 cm) PVC electrically actuated ball valve.

A Tess-Com Model #1940 chloride ion specific electrode and Tess-Com Model #1943 reference electrode were submersed into the fluid in the tank. A Rosemount Model 54e pH/ORP Analyzer/Controller reconfigured by the manufacturer to record chloride ion concentration was connected electrically to the chloride ion specific electrode.

Testing began by flowing water through the test arrangement described above to set the base chloride ion level, which was found to be 28–33 ppm. This value was subtracted from the analyzer values to provide a true chloride ion increase versus free chlorine. ACCUTAB® SI calcium hypochlorite tablets were loaded into the feeder unit. These tablets are 3⅛ inch (7.9 cm) diameter 300-gram tablets commercially available from PPG Industries, Inc. The flow rate of water to the feeder unit was adjusted periodically to give different delivery rates of solutions of calcium hypochlorite. Samples were taken from the submersible pump discharge and analyzed for free available chlorine. The analyzer reading for chloride ion concentration was recorded at the same time. The incoming water chloride ion concentration was subtracted to give a true reading of the level of added chloride ion. Data recorded for this example is found in Table 1.

Runs 2 and 3

The procedure of Run 1 was repeated while varying the flow rate of water to the feeder unit. Results are tabulated in Table 1.

Run 4

The procedure of Run 1 was repeated except that one inch (2.54 cm) diameter, 20-gram Leslie's Power Pro Tabs calcium hypochlorite tablets were charged to the feeder unit in order to obtain higher chloride ion values. The one inch (2.54 cm), 20-gram tablets are commercially available from Leslie's Swimming Pool Supplies, Inc. Results of this Run 4 are tabulated in Table 1.

TABLE 1

| Run 1 | | Run 2 | | Run 3 | | Run 4 | |
|---|---|---|---|---|---|---|---|
| Cl– | FAC | Cl– | FAC | Cl– | FAC | Cl– | FAC |
| 54 | 172 | 35.5 | 135 | 36 | 148.2 | 122 | 362 |
| 33 | 107.4 | 43 | 144 | 41 | 132.4 | 116 | 345 |
| 21 | 71.4 | 6 | 39 | 42 | 130.7 | 77 | 253 |
| 20 | 70.3 | 20 | 72 | 17.5 | 60.3 | 92 | 299 |
| 13 | 45.5 | | | 15 | 53 | 96 | 299 |
| 11 | 37.8 | | | 23 | 83.2 | 97 | 313 |
| 3 | 16.7 | | | 20 | 83.6 | 96 | 297 |
| | | | | 22 | 80.8 | 99 | 301 |
| | | | | 21.5 | 79.9 | 81 | 257 |
| | | | | 21 | 78 | 64 | 191 |
| | | | | 21.5 | 83 | 70 | 222 |
| | | | | 6.5 | 30.5 | 78 | 246 |
| | | | | 5.5 | 29.1 | 81 | 248 |
| | | | | 4 | 26.2 | 115 | 347 |
| | | | | 7 | 45.4 | 70 | 224 |
| | | | | 10 | 42.8 | 62 | 204 |
| | | | | 11.5 | 53.7 | 29 | 102 |
| | | | | 19.5 | 78.8 | 20 | 76 |
| | | | | 37 | 124.6 | 20 | 77 |
| | | | | 36.5 | 118.1 | 21 | 87 |
| | | | | 24 | 103.6 | 72 | 229 |

Cl– (Chloride ion);
FAC (Free Chlorine)

EXAMPLE II

Using the arrangement of equipment and the procedures of Example I, the Rosemount controller was placed in a control mode and set to control the chloride ion concentration between 90 and 100 ppm, which was calculated to yield an actual chloride ion concentration of from 62 to 72 ppm, based on a base chloride ion concentration of 28 ppm for the incoming water. From the graph of FIG. 2, a chloride ion concentration of between 62 and 72 ppm should yield a free chlorine concentration of between 198 and 227 ppm. Seven samples were taken over a 45-minute period in the manner described in Example I and titrated for free available chlorine concentration. The FAC values obtained for the seven samples were: 194, 213, 212, 187, 221, 195 and 206. The average FAC value for these seven samples is 204. The results of Example II show that the free available chlorine concentration in an aqueous medium can be controlled using the chloride ion concentration in that aqueous medium, as determined by a chloride ion specific electrode.

The present invention has been described with reference to specific details of particular embodiments thereof. It is not intended that such details be regarded as limitations upon the scope of the invention except insofar as and to the extent that they are included in the accompanying claims.

What is claimed is:

1. A method for controlling the level of free chlorine in an aqueous fluid comprising the steps of:

a. providing a first aqueous fluid substantially free of free chlorine;

b. providing water-soluble material, which is a source of free chlorine and chloride ion;

c. admixing said first aqueous fluid with water-soluble material, thereby to produce a second aqueous fluid containing free chlorine and chloride ion;

d. measuring the level of chloride ion in said second aqueous fluid by means of a chloride ion specific sensor; and e. controlling, if necessary, in response to the measurement of step (d) the level of free chlorine in said second aqueous fluid by the further steps of (i) adjusting the amount of first aqueous fluid admixed with the water-soluble material, (ii) diluting said second aqueous fluid with aqueous fluid substantially free of free chlorine, or (iii) a combination of steps (i) and (ii).

2. The method of claim 1 wherein the first aqueous fluid is water.

3. The method of claim 1 wherein the water-soluble material is alkali metal hypochlorite, alkaline earth metal hypochlorite, chloride ion-containing hypochlorous acid, chloride ion-containing halo-substituted hydantoins, chloride ion-containing chlorinated isocyanurates, or the alkali metal salts of chloride ion-containing dichloroisocyanurates.

4. The method of claim 3 wherein the alkaline earth metal hypochlorite is a solid.

5. The method of claim 3 wherein the alkali metal hypochlorite is sodium hypochlorite or lithium hypochlorite, the alkaline earth metal hypochlorite is calcium hypochlorite, the chloride ion-containing hypochlorous acid is the reaction product of chlorine and water, the halo-substituted hydantoin is bromo-chloro dimethyl hydantoins or dichlorohydantoin, and the chlorinated isocyanurates are trichloroisocyanurate and dichloroisocyanurate.

6. The method of claim 5 wherein the calcium hypochlorite is in a solid form.

7. The method of claim 5 wherein the first aqueous fluid is water and the first aqueous fluid and water-soluble material are admixed in a mixing vessel, thereby to produce said second aqueous fluid.

8. The method of claim 5 wherein the alkali metal hypochlorite is an aqueous solution of sodium hypochlorite containing from 12 to 15 percent available chlorine.

9. The method of claim 1 wherein step (e) is assisted by means of controller means in electrical contact with said chloride ion specific sensor, said controller means being also in electrical contact with valve control means associated with the flow of first aqueous fluid.

10. The method of claim 1 wherein the aqueous fluid used in step (e)(ii) is first aqueous fluid.

11. A method of sanitizing an aqueous medium, comprising mixing second aqueous fluid prepared by the method of claim 1 with said aqueous medium.

12. The method of claim 11 wherein the aqueous medium is drinking water, cooling water, wastewater, or a recreational body of water.

13. A method of sanitizing the surface of an article requiring sanitizing, comprising contacting said surface with second aqueous fluid prepared by the method of claim 1.

14. A method for controlling the amount of free chlorine in an aqueous fluid comprising the steps of:

a. providing a water-soluble material that is a source of free chlorine and chloride ion within a mixing vessel;

b. providing a first aqueous fluid that is substantially free of free chlorine;

c. introducing first aqueous fluid into said mixing vessel, thereby to admix said first aqueous fluid with water-soluble material and produce second aqueous fluid containing free chlorine and chloride ion;

d. removing second aqueous fluid from said mixing vessel;

e. determining the concentration of chloride ion in second aqueous fluid removed from said mixing vessel by means of a chloride ion specific electrode; and f. controlling, if necessary, in response to the analysis of step (e), the amount of free chlorine in second aqueous fluid removed from the mixing vessel around a preselected value by the further steps of (i) adjusting the rate at which first aqueous fluid is introduced into said mixing vessel, (ii) adding aqueous fluid substantially free of free chlorine to second aqueous fluid removed from the mixing vessel, or (iii) a combination of steps (i) and (ii).

15. The method of claim 14 wherein the water-soluble material in the mixing vessel is alkali metal hypochlorite, alkaline earth metal hypochlorite, chloride ion-containing hypochlorous acid, chloride ion-containing halo-substituted hydantoins, chloride ion-containing chlorinated isocyanurates, or the alkali metal salts of chloride ion-containing dichloroisocyanurate, and the first aqueous fluid is water.

16. The method of claim 15 wherein the alkali metal hypochlorite is sodium hypochlorite or lithium hypochlorite, the alkaline earth metal hypochlorite is calcium hypochlorite, the chloride ion-containing hypochlorous acid is the reaction product of chlorine and water, the halo-substituted hydantoin is bromo-chloro dimethyl hydantoins or dichlorohydantoin, and the chlorinated isocyanurates are trichloroisocyanurate and dichloroisocyanurate.

17. The method of claim 16 wherein the alkaline earth metal hypochlorite is a solid form of calcium hypochlorite.

18. The method of claim 17 wherein the solid calcium hypochlorite is in the form of tablets.

19. The method of claim 14 wherein step (f) is assisted by means of controller means in electrical contact with said chloride ion specific electrode, said controller means being also in electrical contact with valve control means associated with the flow of said first aqueous fluid.

20. The method of claim 19 wherein said controller means is a microprocessor or a programmable logic controller.

21. The method of claim 14 wherein the aqueous fluid of step (f)(ii) is first aqueous fluid.

22. The method of claim 19 wherein the chloride ion specific sensor sends an electrical signal to said controller means, which in turn sends an electrical signal to said valve control means, which adjusts the flow of first aqueous fluid introduced into the mixing vessel.

23. The method of claim 22 wherein said valve control means increases the flow of first aqueous fluid into said mixing vessel, thereby increasing the amount of chloride ion and free chlorine in second aqueous fluid removed from said mixing vessel.

24. The method of claim 22 wherein said valve control means decreases the flow of first aqueous fluid into said mixing vessel, thereby decreasing the amount of chloride ion and free chlorine in second aqueous fluid removed from said mixing vessel.

25. A method for monitoring and adjusting free chlorine levels in an aqueous fluid comprising the steps of:

a. providing a first aqueous fluid substantially free of free chlorine;

b. providing in a mixing vessel a water-soluble material that is a source of free available chlorine and chloride ion;

c. introducing controllably first aqueous fluid into said mixing vessel and into contact with water-soluble material, thereby to produce second aqueous fluid containing free chlorine and chloride ion;

d. withdrawing second aqueous fluid from said mixing vessel and forwarding second aqueous fluid to a holding vessel;

e. measuring the concentration of chloride ion in second aqueous fluid contained in said holding vessel by means of a chloride ion specific electrode; and f. controlling, if necessary, in response to the measurement of step (e) the level of free chlorine in second aqueous fluid in said holding vessel by the further steps of (i) adjusting the rate at which first aqueous fluid is introduced into said mixing vessel, (ii) diluting second aqueous fluid in said holding vessel with aqueous fluid substantially free of free chlorine, or a combination of steps (i) and (ii).

26. The method of claim 25 wherein the water-soluble material that is the source of free chlorine and chloride ion is alkaline earth metal hypochlorite and the first aqueous fluid is water.

27. The method of claim 26 wherein the alkaline earth metal hypochlorite is a solid form of calcium hypochlorite.

28. The method of claim 27 further comprising the steps of:

a. establishing a desired concentration of chloride ion for second aqueous fluid in said holding vessel;

b. providing controller means in electrical contact with said chloride ion specific electrode;

c. providing flow control means in association with the flow of first aqueous fluid into the mixing vessel, which flow control means is also in electrical contact with said controller means; and d. adjusting, if required, the flow of first aqueous fluid into said mixing vessel by said flow control means.

29. The method of claim 28 wherein the flow control means is an electrically actuated valve.

30. The method of claim 28 wherein said controller means is a microprocessor.

31. The method of claim 28 wherein said controller means is a programmable logic controller.

32. The method of claim 29 wherein the electrically actuated valve is a three-way valve.

33. The method of claim 25 further comprising the step of providing liquid communication between the source of first aqueous fluid and said holding vessel, thereby to allow the introduction of first aqueous fluid into said holding vessel.

34. The method of claim 25 wherein the aqueous fluid used in step (f)(ii) is first aqueous fluid.

35. The method of claim 28 further providing flow control means controlling the flow of first aqueous fluid to said holding vessel, said flow control means being in electrical contact with said controller means.

* * * * *